United States Patent [19]

Casale

[11] Patent Number: 4,944,733
[45] Date of Patent: Jul. 31, 1990

[54] DIAPER FOR USE IN TOILET TRAINING MALE CHILDREN OR FOR USE BY INCONTINENT MALE ADULTS

[76] Inventor: Larry Casale, 2092 Webster Dr., Park City, Utah 84060

[21] Appl. No.: 364,641

[22] Filed: Jun. 12, 1989

[51] Int. Cl.⁵ .............................................. A61F 13/16
[52] U.S. Cl. ...................................... 604/385.1; 2/405
[58] Field of Search ............... 604/386, 389, 390, 391, 604/392, 393, 394, 401, 385.1; 2/80, 82, 83, 400, 405

[56] References Cited

U.S. PATENT DOCUMENTS

| | | | |
|---|---|---|---|
| 2,214,578 | 9/1940 | Davis | 2/405 |
| 2,473,692 | 6/1949 | Murphy | 2/405 |
| 3,508,550 | 4/1970 | Vollrath | 604/394 |
| 3,714,946 | 2/1973 | Rudes | 604/394 |
| 3,768,481 | 10/1973 | Shibata | 604/394 |
| 4,145,763 | 3/1979 | Abrams et al. | 604/391 |
| 4,205,679 | 6/1980 | Repke | 2/402 |
| 4,230,113 | 10/1980 | Mehta | 604/385.1 |
| 4,326,302 | 4/1982 | Lowe et al. | 2/404 |
| 4,589,877 | 5/1986 | Sivilich | 604/385.1 |
| 4,610,680 | 9/1986 | La Fleur | 604/385.1 |
| 4,615,695 | 10/1986 | Cooper | 604/385.1 |
| 4,627,846 | 12/1986 | Ternström | 604/385.1 |
| 4,675,015 | 6/1987 | Brown | 604/385.1 |
| 4,695,279 | 9/1987 | Steer | 604/401 |
| 4,743,239 | 5/1988 | Cole | 604/385.1 |

Primary Examiner—C. Fred Rosenbaum
Assistant Examiner—Sharon Rose

[57] ABSTRACT

A diaper/incontinent device for children or adults is disclosed. The diaper comprises a front portion and a back portion connected by a crotch portion, the crotch portion includes leg openings which allow the diaper to be attached around the legs and waist of the user. The front portion of the diaper further includes a reclosable penile opening which extends from the waist opening through the center of the front portion down into the crotch portion of the diaper. The opening ins held closed by tape fastener or the like. The penile opening comprises a pair of flaps which overlap each other in a closed position and which can be pulled apart to allow the user to urinate therethrough in an open position. The opening can then be reclosed and/or resealed. The penile opening can be advantageously formed without otherwise disturbing the secure attachment of the diaper around the user's legs and waist. The diaper is therefore useful for purposes of potty training a male child or for protection of adult males having incontinence problems. The diaper can be used with an ordinary pair of pants, and avoids the necessity of removal of pants and/or diaper for normal urination, allowing the wearer to use a urinal or toilet in the conventional manner.

6 Claims, 5 Drawing Sheets

DIAPER FOR USE IN TOILET TRAINING MALE CHILDREN OR FOR USE BY INCONTINENT MALE ADULTS

BACKGROUND OF THE INVENTION

1. Field of the Invention.

This invention relates to an absorbent garment useful for infants, children and adults. More particularly, this invention relates to a diaper useful as a potty training device for male children and/or as an incontinent device for male adults.

2. Background of the Invention.

It is known to provide disposable diapers for infants having construction with varying thicknesses of disposable material generally made in a rectangular form for positioning on the infant's body. It is also known to provide disposable material made in a generally rectangular form for positioning on the body of an adult who has an incontinency problem which requires the use of an absorbent garment.

Presently, diapers comprise an absorbent pad, usually formed of layers of material, having a tab on each side of one end of the diaper which is adapted to securely attach to the other end thereof when it has been wrapped around a child. These diapers also usually include an absorbent inner layer and an outer layer of nonabsorbent plastic material. Most of these types of diapers are intended to be thrown away after each use and are not intended for repeated removal and replacement on the child. When a child is of an age when he is undergoing potty training, the continued necessity of removing and thus destroying clean diapers in order to allow the child to be trained in using the toilet, causes significant problems. First, many times a new diaper must be placed on the child after each use of the toilet causing significant expense in unsoiled discarded diapers. Second, a male child that is at the age of potty training is generally incapable of removing and refreshing a diaper by himself. The child must therefore awaken his parents at night in order to urinate in the toilet, since their help is required for removing and replacing the diaper. Third, in the case of both male children and incontinent male adults, present diaper constructions do not allow for urination in standing urinals as are commonly used in public restroom facilities. For example, instead of being able to urinate through the fly or opening in a pair of pants, the entire pant and diaper must be removed to allow for urination. This requirement can cause extreme embarrassment to the user when in a public facility.

Therefore, a need exists for a diaper which can be securely attached to a user's legs and waist, yet can be quickly and easily opened at the front to allow the male user to urinate therethrough in the common manner. Such a diaper must also be able to remain securely attached to the user while the opening is being used, and the opening must be completely and easily reclosable and resealable against leakage.

A modified form of a disposable diaper is disclosed in U.S. Pat. No. 4,610,680 to LaFleur in which a disposable diaper usable for either males or females comprises an opening device having a string, or loop and hook fastening members, which allow the garment to be torn away from or otherwise completely unwrapped from the child's legs without manipulation of the child's body through the waist and/or leg openings.

U.S. Pat. No. 4,589,887, to Sivilich discloses a male incontinent shield which must be attached to the user's undergarments and which has a slit placed in the central portion thereof, the slit allowing the male user to leave the shield in place in the undergarment while urinating therethrough.

U.S. Pat. No. 4,615,695 to Cooper discloses a training pant with a water absorbable material therein, the pant having the shape of an ordinary pair of briefs and being detachable from the body by means of loop and hook fasteners located between the waist and leg openings.

None of the above prior art devices provides a male user with the ability to easily open the front of a diaper from the center of the front waist portion thereof, down to the center of the crotch portion, to allow for easy urination through the front of the diaper (and the fly of a pair of pants) and then to quickly and easily reseal the opening, all while having the diaper remain securely fastened around the legs and securely held in place such that readjustment or replacement is not required, and such that an undergarment or the like is not required.

SUMMARY OF THE INVENTION

It is an object of the present invention to provide a reusable absorbent device for incontinent males or male children.

It is further an object of the invention to provide a diaper which is securely self-attachable around the legs and waist of the user, yet which allows the front of the diaper to be opened for urination therethrough and then reclosed.

It is further an object of the invention to provide a method of making the above-described device.

The above and other objects of the invention are realized in an illustrative embodiment of a diaper which advantageously includes an inner water permeable layer, an outer nonabsorbent layer, and an absorbent padding positioned between the inner and outer layers. The diaper may be formed in a generally hourglass shape having fastening tabs to secure the diaper around the legs and waist of the user. In one embodiment of the invention the diaper contains an opening, which extends from a waist section through a front portion and into a crotch portion thereof, which has overlapping flaps which are sealed in a closed position by a reusable tape fastener. The flaps are separable to form a penile opening, and then reclosable and resealable.

The diaper is formed by cutting the absorbent padding in a generally hourglass shape, the hourglass shape defining a front portion, a crotch portion and a back portion with the front portion having a generally triangular shaped notch formed therein which extends into the crotch portion, and then bringing together the subsequent edges of the notch until they form an overlapping pair of flaps. The absorbent pad may be enveloped between an outer nonabsorbent layer of plastic material and an inner water permeable layer of material. Also, the inner water permeable layer may extend around the overlapped portion of the inner flap, thus allowing the padding in the inner flap to absorb water from both of its sides.

In one preferred embodiment of the invention, the flaps are generally rectangular in shape and are made of a reduced thickness of padding so that in their overlapped configuration they do not form an excessive thickness of material. The flaps may also advantageously be generally triangular in shape, causing them to overlap to a greater extent at the waist or front portion, than at the crotch portion.

The reusable tape fastener may be attached to the outer flap and to the outer surface of the front portion of the diaper. The tape fastener may extend along a portion of the edge of the outer flap, or may extend along the entire length of the outer flap entirely sealing the edge thereof to the front portion of the diaper.

In a further embodiment, a second reusable tape fastener may be located in between the flaps and may be covered with a removable plastic strip. This second fastener would then become useful at any time in which the original fastener becomes soiled, or is otherwise incapable of resealing the flaps in their closed position. The second fastener would be used by removing the plastic cover strip and thereafter pressing the overlapping flaps together.

The present invention provides a diaper which can be worn in a manner substantially similar to other well-known type disposable diapers, yet may be easily opened in the front thereof (such as through the fly of a pair of pants) without causing the diaper to misposition or disassemble. The user may then urinate therethrough, and then may reclose or reseal the opening to prevent leakage.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Figure 1:
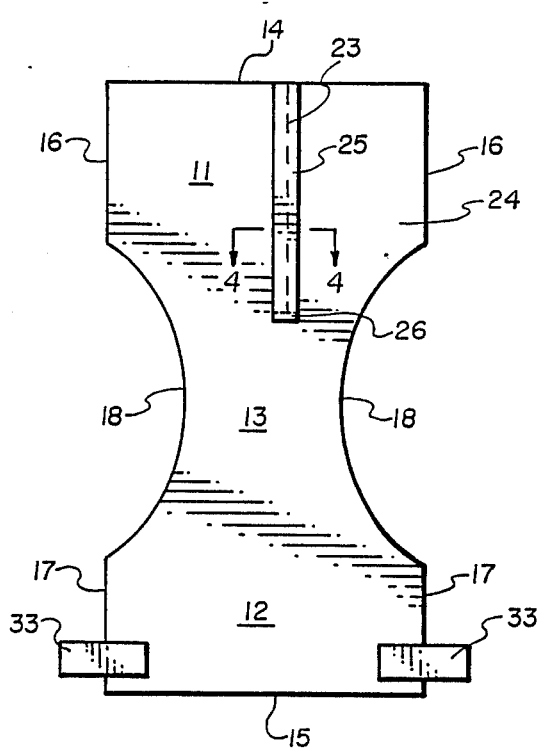
FIG. 1 shows a plan view of the outer surface of a diaper according to the present invention.

Referring now to the drawings in which similar elements
the same number in each of the various figures, FIG. 1 shows a plan view of the exterior surface of a diaper 10 of the invention showing the positioning of the various portions thereof which include: a front portion 11, a back portion 12 and a crotch portion 13.

The front portion 11 comprises a front waist section 14 and front side sections 16. The back portion 12 comprises a back waist section 15 and back side sections 16. The crotch portion 13 connects the front portion 11 and the back portion 12 and comprises leg sections 18. The entire exterior surface being covered with an outer layer 24 of nonabsorbent material.

Figure 2:
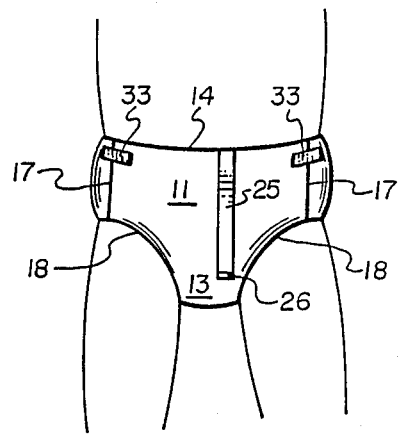
FIG. 2 shows a perspective view of the diaper according to the present invention positioned on a user.

Referring now to FIG. 2 of the drawings, there is shown diaper 10 attached around the legs and waist of a user with fastening tapes 33 being secured to side sections 16 in a well-known manner.

Figure 3:
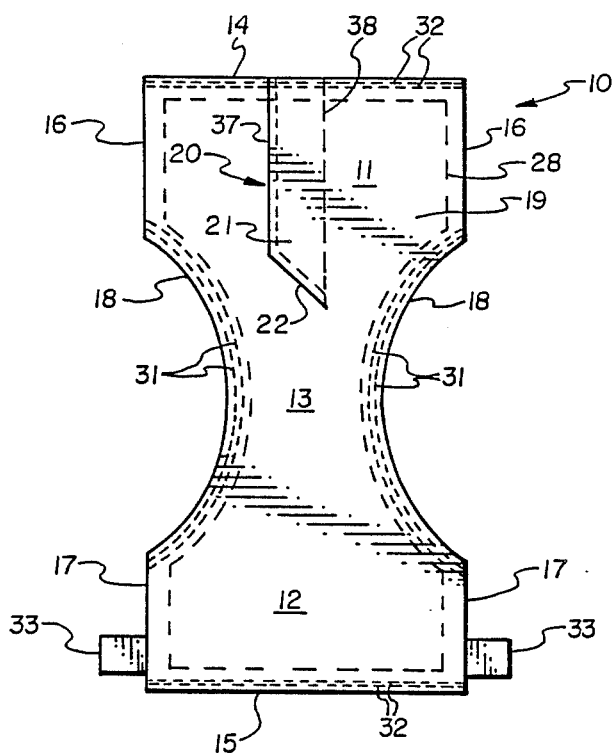
FIG. 3 is a plan view of the interior surface of the diaper according to the invention.

FIG. 3 shows a plan view of the inside surface of the diaper 10. The entire inside surface being covered with a water permeable inner layer 19. Leg elastics 31 and waist elastics 32 are secured in between the inner layer 19 and outer layer 24 so as to be located around the legs and waist of the user in order to prevent leakage when the diaper is in place. The absorbent padding layer 28 is located in between the inner layer 19 and outer layer 24 and is held therein by the secure attachment of the inner and outer layers 19 and 24 respectively around their entire periphery thereof, and/or by adhesives as is well-known in the art of diaper manufacture.

The outer nonabsorbent layer 24 may be made of any commonly used materials such as a 0.6 mil. polyethylene or polypropylene film. The inner water permeable layer 19 may be made of any material useful for this purpose, such as a lightweight nonwoven fabric of polyester or polyethylene. The intermediate absorbable padding layer 28 may comprise one or more layers of one or more type of absorbent material commonly used for such purposes such as absorbent fibers, absorbent wadding, super absorbent powder or granules, etc. The fastening strips may also comprise commonly materials including but not limited to impermeable sheets having an adhesive thereon such as pressure sensitive hot melt-/release paper, water or solvent based pressure sensitive adhesive/release paper, or double-sided tape.

The above features of the diaper of the present invention are illustrative only of the diaper constructions of the prior art. It is here noted that any prior art diaper similar to the above may be adapted for use with the present invention.

The urination opening 20 is located in the front portion 11 of the diaper 10 and comprises an interior flap 21 which extends from the front waist section 14 into the crotch portion 13 (having cutaway section 22 of flap 21 located in crotch portion 13), and an exterior flap 23 which also extends from waist section 14 into the crotch portion 13.

Figure 4:
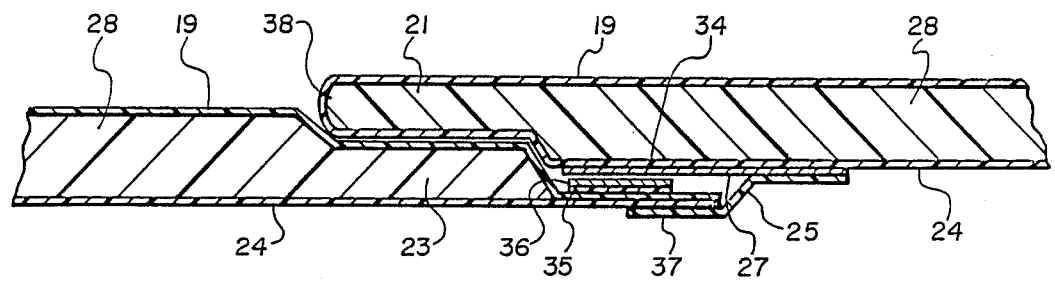
FIG. 4 is a cross-sectional view of a diaper according to the present invention taken along line 4—4 of FIG. 1.

As is best seen in FIG. 4, the flaps 21 and 23 are held in a closed position by fastening tape 25. The fastening tape 25 is removably secured to the attachment strip 27, and is permanently secured to the portion of impermeable layer 24 which comprises the edge of flap member 23. If desired, end 26 of tape 25, can also be permanently attached to impermeable surface 24. Thus when flap 23 is separated from flap 21 to form the penile opening, tape fastener 25 will separate from its attachment to strip 27 until it is prevented from separating further by the end 26.

The portions of intermediate layer 28 which make up the inner flap 21 and outer 23, may be advantageously made of a slightly reduced thickness so that in their overlapped configuration, they substantially equal, or are at least less than twice the thickness of the remainder of the intermediate absorbent padding layer 28, in order to avoid significant bulging in their overlapping area.

The outer nonabsorbent cover layer 24 extends slightly beyond the flap 23 and is permanently attached to tape fastener 25 along the length of its edge 37. Outer nonabsorbent cover layer 24 stops short of extending to the edge 38 of flap 21, and is met by the inner absorbent cover layer 19 which extends completely around edge 38 of flap 21 to join therewith at connection 34.

Attaching strip 27 is located over the connection 34 between outer nonabsorbent cover layer 24 and inner absorbent cover layer 19 and comprises a coating on the outer surface thereof which will releasably secure tape fastener 25. In use, when it is desired to open penile opening 20, flap members 23 and 21 are pulled apart from each other causing tape fastener 25 to pull away from the surface of attaching strip 27. When it is desired to reclose the opening, flaps 23 and 21 are replaced in their overlapping position and tape fastener 25 is again pressed against attaching strip 27.

As shown in FIG. 4, an additional tape fastener 29 may be adhesively attached to the interior side of the portion of outer nonabsorbable cover layer 24 extending beyond the flap 23, and be covered with a cover strip 30. Thus when in use, if tape fastener 25 accidentally becomes soiled or is for any other reason unable to be reattached to attaching strip 27, cover strip 30 may be removed from tape fastener 29 to expose a new adhesive surface, and fastener 29 can be secured to attaching strip 27. Tape fastener 29 may be of any shape; advantageously, however, it may extend the length of the overlapping portions of flaps 21 and 23.

Figure 5:
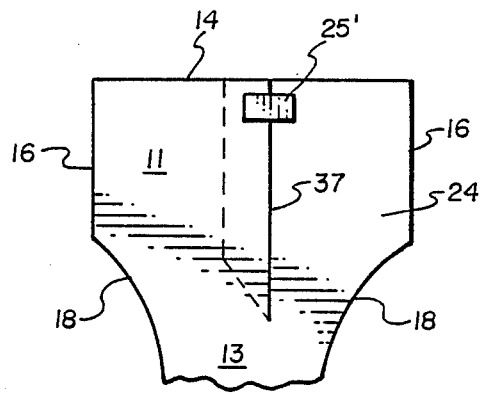
FIG. 5 is a plan view of a portion of the exterior surface of the diaper according to another embodiment of the invention.

FIG. 5 shows another preferred embodiment of the invention which comprises opening 20 having flap members 21 and 23 of generally rectangular shape and a tape fastener 25' which extends across the edge 37 of flap 23 to fasten the flaps 21 and 23 together in much the same fashion as is commonly done to attach side sections of the diaper around the user's legs.

Figure 6:
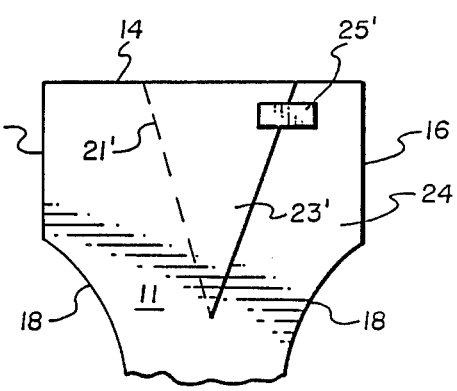
FIG. 6 shows a plan view of a portion of the exterior surface of the diaper according to another embodiment of the invention.

FIG. 6 shows a further preferred embodiment of the opening 20 wherein the flaps 21' and 23' are generally triangular in shape having their largest overlapping in the area of waist section 14 and their smallest overlapping in the crotch portion 13.

Figure 7:
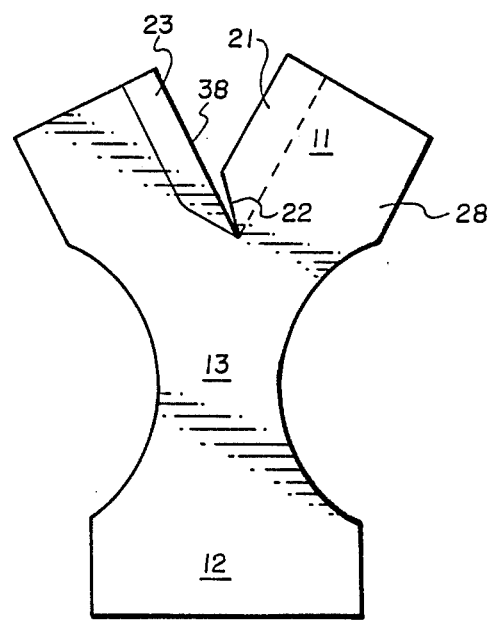
FIG. 7 shows a plan view of the absorbent material portion of the diaper according to the invention.

FIG. 7 shows a plan view of intermediate absorbent padding layer 28 as it may be stamped or otherwise cut to form the diaper of the present invention. The back portion 12 is cut to be shapable around the back of the user's body such as is well-known, and the front portion 11 is formed of a wider section of padding having in the center thereof a generally triangular shaped notch. The portions of the padding which border the notch being used to generate the flaps 21 and 23 and being made slightly thinner than the remaining padding layer 28. Inner permeable cover layer 19 and outer nonabsorbent cover layer 24 can then be placed around the absorbent padding 28 to seal it therein in the conventional manner. The diaper may also include elastic members 31 and 32 located in between the inner and outer layers at the leg sections 18 and front and back waist sections 14 and 15 respectively. The inner and outer cover layers can also extend beyond the edge 37 of outer flap 23, while the inner absorbent cover layer 19 may extend around the inner flap 21.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

I claim:

1. A diaper for attachment around the waist and legs of a user consisting of a pad means having a front portion for placement over the groin area of a user, a back portion for placement about the buttocks of a user and a crotch portion for placement between the user's legs, said crotch portion connecting said front and back portions, said front portion having a top edge and side edges, and said back portion having a top edge and side edges, said front portion side edges and said back portion side edges being interattachable about a user's legs, said front portion top edge and said back portion top edge forming a continuous edge about the user's waist when said front and back portion side edges are interattached about the user's legs, said front portion top edge having a central section located generally centrally between said front portion side edges, attaching means for interattaching said front portion side edges with said back portion side edges, first and second flap means extending from said central section of said front portion top edge into said crotch portion, said first and second flap means being movable from a first position forming an adjacent overlapping closure, to a second position forming a penile opening, and a first adhesive fastening means for removably fastening said first flap to said second flap in said overlapping position.

2. A diaper according to claim 1 wherein said pad means further includes an outer nonabsorbent cover layer, an inner moisture permeable layer, and an intermediate absorbent padding layer, said intermediate absorbing padding layer being located in between said outer nonabsorbent cover layer and said inner moisture permeable layer.

3. A diaper according to claim 1 consisting further of a second adhesive fastening means which is located between said first and second flap means when said first and second flap means are in said overlapping position.

4. A diaper according to claim 2 wherein said first and second flap means include portions of said intermediate absorbent padding layer, the thickness of each portion of said intermediate absorbent padding layer which form said first and second flap means being less than the thickness of the portions of said intermediate absorbent padding layer which is adjacent to said first and second flap means.

5. A diaper according to claim 4 in which said first flap means includes a portion of said outer nonabsorbent cover layer, a portion of said intermediate absorbent padding layer, and a portion of said inner moisture permeable layer, and said second flap means comprises a portion of said intermediate absorbent padding layer surrounded by said inner moisture permeable layer.

6. A diaper according to claim 3 wherein said second adhesive fastening means is secured to said first flap means and comprises an adhesive tape covered with a cover strip, whereby when said first adhesive fastening means said first flap to said second flap becomes soiled or is otherwise no longer capable of fastening said first flap to said second flap, said cover strip may be removed from said second adhesive fastening means and said second adhesive fastening means may be used to removably fasten said first flap to said second flap in said overlapping position.

* * * * *